US012638386B2

(12) United States Patent
Roy et al.

(10) Patent No.: US 12,638,386 B2
(45) Date of Patent: May 26, 2026

(54) CANCER DIAGNOSTIC

(71) Applicant: MetroDTx Ltd, London (GB)

(72) Inventors: Debdulal Roy, Swansea (GB); Edward Duckworth, Swansea (GB); Bilal Al-Sarireh, Swansea (GB)

(73) Assignee: MetroDTx Ltd, London (GB)

( * ) Notice: Subject to any disclaimer, the term of this patent is extended or adjusted under 35 U.S.C. 154(b) by 166 days.

(21) Appl. No.: 18/289,925

(22) PCT Filed: May 10, 2022

(86) PCT No.: PCT/EP2022/062648
§ 371 (c)(1),
(2) Date: Nov. 8, 2023

(87) PCT Pub. No.: WO2022/238407
PCT Pub. Date: Nov. 17, 2022

(65) Prior Publication Data
US 2024/0280482 A1     Aug. 22, 2024

(30) Foreign Application Priority Data
May 12, 2021    (GB) ..................................... 2106730

(51) Int. Cl.
*G01N 21/35* (2014.01)
*G01N 1/40* (2006.01)
(Continued)

(52) U.S. Cl.
CPC ....... *G01N 21/3577* (2013.01); *G01N 1/4077* (2013.01); *G01N 33/487* (2013.01);
(Continued)

(58) Field of Classification Search
CPC . G01N 21/3577; G01N 1/4077; G01N 33/487
See application file for complete search history.

(56) References Cited

U.S. PATENT DOCUMENTS 9,664,680 B2      5/2017  Baker et al.
2010/0241357 A1*  9/2010  Chan ...................... G01N 21/65
                                          702/179
(Continued)

OTHER PUBLICATIONS

Ferreira et al, "Attenuated Total Reflection-Fourier Transform Infrared (ATR-FTIR) Spectroscopy Analysis of Saliva for Breast Cancer Diagnosis," *J Oncol.* vol. 2020, Article ID 4343590, 11 pages, 2020.
(Continued)

*Primary Examiner* — Hugh Maupin
(74) *Attorney, Agent, or Firm* — Klarquist Sparkman, LLP

(57) ABSTRACT
The invention concerns a method for determining a preferred fraction of a biological sample for use in a method for diagnosing cancer in a subject and the use of the identified fraction of a sample in a further method comprising performing FTIR spectral analysis of the identified fraction of the sample obtained from the subject and, optionally, comparing the same fraction of a control or reference sample to indicate those subjects with increased likelihood of disease; use of said method to further select a course of treatment for cancer and a method of treatment comprising same.

22 Claims, 8 Drawing Sheets

Figure 1:
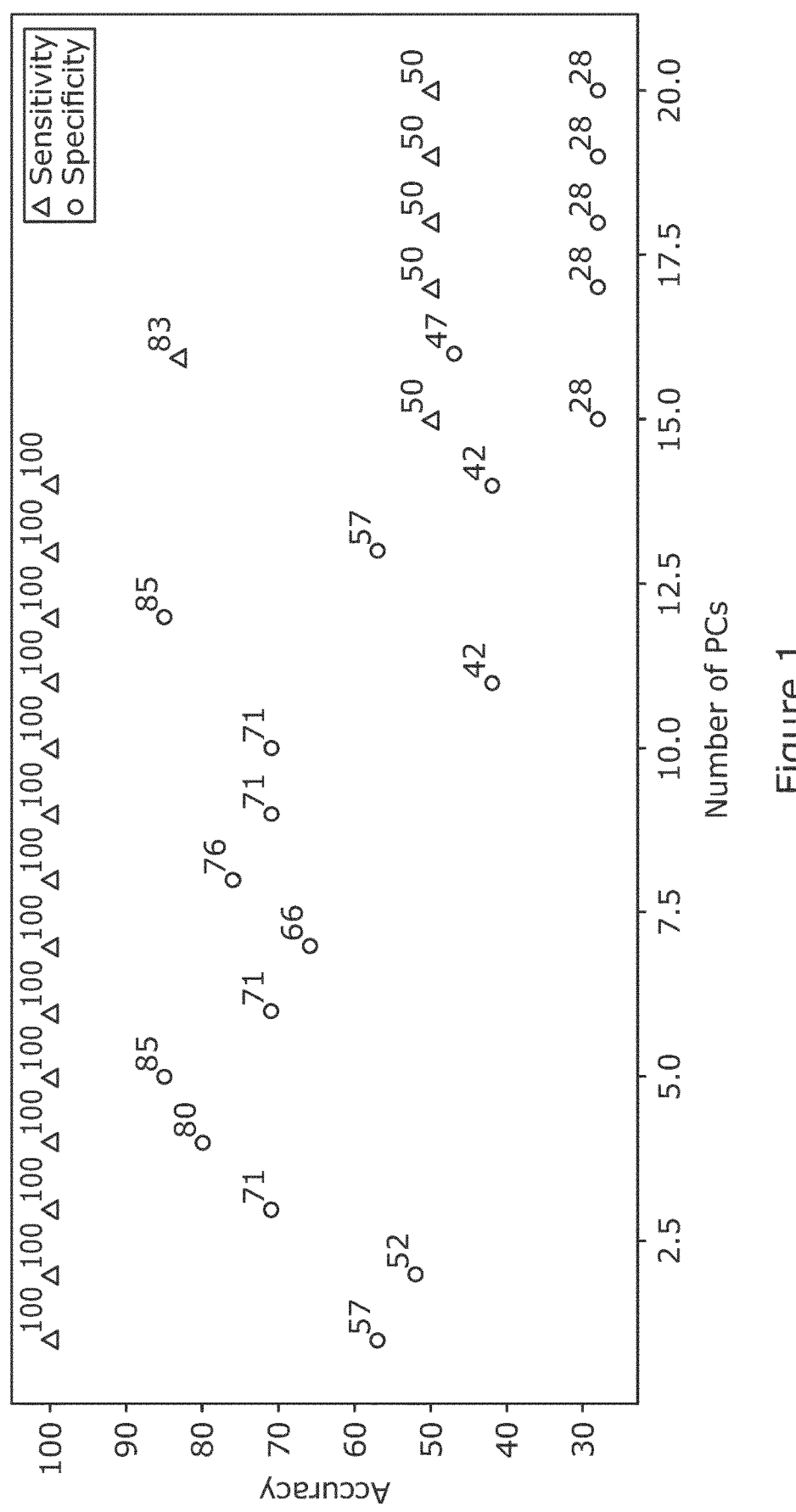

(51) Int. Cl.
    *G01N 21/3577*     (2014.01)
    *G01N 33/487*     (2006.01)
(52) U.S. Cl.
    CPC ................ *G01N 2001/4088* (2013.01); *G01N 2021/3595* (2013.01)

(56)            References Cited

U.S. PATENT DOCUMENTS

| | | | | |
|---|---|---|---|---|
| 2015/0301017 A1* | 10/2015 | Baker | .................. | G01N 33/574 |
| | | | | 436/171 |
| 2021/0156862 A1* | 5/2021 | Holman | ........... | G01N 33/57449 |
| 2021/0247301 A1* | 8/2021 | Baker | .................. | G01N 33/487 |
| 2022/0308058 A1* | 9/2022 | Baker | .................... | G01N 21/35 |

OTHER PUBLICATIONS

Hands et al, "Investigating the rapid diagnosis of gliomas from serum samples using infrared spectroscopy and cytokine and angiogenesis factors," *Anal Bioanal Chem.* 405:7347-7355, 2013.
Rai et al, "Serum-based diagnostic prediction of oral submucous fibrosis using FTIR spectrometry," *Spectrochimica Acta Part A: Molecular and Biomolecular Spectroscopy* 189:322-329, 2017.
Santillan et al, "Discrimination of malignant from benign thyroid lesions through neural networks using FTIR signals obtained from tissues," *Anal Bioanal Chem.* 413:2163-2180, 2021.
International Search Report mailed on Sep. 19, 2022 in PCT/EP2022/062648, 4 pages.
Written Opinion mailed on Sep. 19, 2022 in PCT/EP2022/062648, 7 pages.
Search Report dated Feb. 10, 2022 in GB 2106730.1 (2 pages).

* cited by examiner

CANCER DIAGNOSTIC

CROSS REFERENCE TO RELATED APPLICATIONS

This is the U.S. National Stage of International Application No. PCT/EP2022/062648, filed May 10, 2022, which was published in English under PCT Article 21(2), which in turn claims the benefit of GB Application No. 2106730.1, filed May 12, 2021. The PCT application is incorporated herein in its entirety.

FIELD OF THE INVENTION

The invention concerns a method for determining a preferred fraction of a biological sample for use in a method for diagnosing cancer in a subject and the use of the identified fraction of a sample in a further method comprising performing FTIR spectral analysis of the identified fraction of the sample obtained from the subject and, optionally, comparing the same fraction of a control or reference sample to indicate those subjects with increased likelihood of disease; use of said method to further select a course of treatment for cancer and a method of treatment comprising same.

BACKGROUND OF THE INVENTION

The ability to detect cancers at an early stage has a dramatic effect on the cost of treating the disease, for example early stage colon cancer treatment costs can increase nearly fourfold when having to treat at a late stage. The idea of being able to screen oneself quickly and effectively for disease is a tempting one, as current cancer screening processes have multiple week waiting times for a multitude of symptom tests which may or may not lead to a diagnosis. Radiology and endoscopy are often used, but often these require use of secondary care investigations from specialists that can be unsustainably expensive, especially for an aging population that will require more and more screening. All these point to a need for fast, cheap non-invasive and easy methods for cancer screening.

Vibrational spectroscopic methods rely on the principle that molecules, and primarily the bonds binding them together, absorb light. In particular absorption in the visible to microwave region (e.g. approximately 400 nm to 1 mm in wavelength) are most typically of interest. Specific features of a molecule absorb light of characteristic wavelengths, and by detecting which wavelengths have been absorbed to what degree, one can make deductions about a particular mixture's composition.

Infra-red (IR) absorbance spectroscopy looks at the absorbance of a sample in the infrared region of the electromagnetic spectrum. It achieves this by projecting monochromatic infrared light at a sample. At some infra-red wavelengths, features of molecules in the sample will absorb the radiation, transferring the energy into bond vibrations of the same frequency as the photon absorbed. The absorption is measured over a whole range of wavelengths of infrared light. By knowing the characteristic absorption regions, one can discern the presence of certain structures and even fully characterise the molecules in the sample from the produced spectra. Fourier transform infra-red spectroscopy (FTIR) is a form of IR spectroscopy for sampling a whole range of wavelengths at once, dramatically speeding up the process of analysing a sample over a large range of the infra-red spectrum. It also allows overall light levels to be higher, improving the signal to noise ratio. It achieves this by guiding the light through an interferometer before or after the sample. This alters the distribution of light and produces a signal called an interferogram. This interferogram can be analysed using a mathematical process known as a Fourier transform, which converts it into a readable absorbance spectrum for the sample.

In contrast, Raman spectroscopy focuses on the visible and near-IR light region. When light is shone upon a transparent sample, its oscillating electric field can act on the charges of a particle, the photon being absorbed and causing the charges to move at the same frequency. This energy is emitted as another photon. Typically these emitted photons will have the same frequency as the original, but a small fraction (~1 in 10 million) will be different. This occurrence is inelastic scattering as the light is scattered, but the energy is changed and is termed Raman scattering after its discoverer. In a Raman spectrometer, monochromatic visible lasers are used to probe a sample and the inelastic scattering it exhibits is measured in order to discern features in its molecular structure. The data produced is a spectra of 'Raman shift', which is calculated as the difference between the wavenumbers of the laser and the detected light. Like in Infrared spectroscopy, the Raman shift is presented in units of wavenumber, and the peaks sometimes occur at similar wavenumber positions as in the Infrared spectrum. However, different regions will be highlighted to different magnitudes and in symmetrical molecules with a centre of inversion a signal will only be present in one.

Blood is a particularly useful bio-fluid for inspection due to presence of released protein, nucleic acids, lipids, and their fragments—as changes in these levels are the some of the best indicators of disease. Much of the current research is focused on subsets of blood, the plasma and serum. In whole blood, haemoglobin and other red blood cell associated molecules can interfere with the spectra, so the plasma is preferred as the variable protein concentrations within are more sensitive to disease. Serum is a subset of plasma without the coagulating factors for easier storage and use. Without these natural coagulants present, other de-coagulating chemicals do not need to be added.

Much of the investigation of the vibrational spectroscopy of blood plasma and serum for the purposes of diagnosing and screening of disease are proof-of-principle studies. These typically demonstrate the potential of FTIR or Raman spectroscopy to distinguish between diseased healthy samples on a relatively small sample set. Of these studies, many of them are investigating cancers in the attempt to distinguish characteristic spectral biomarkers for them.

However, whilst vibrational spectroscopic methods more generally as means discern between cancerous and healthy patients has been a popular field of study in recent years, due to lack of transferability of the results, little of this has impacted the clinical setting. Further, it is not always clear why either FTIR or Raman methods are chosen for the study of a particular disease, or in what context one technique has superiority over the other.

There is therefore also clearly an unmet need for an improved cancer diagnostic tool and refinement of vibrational spectroscopic analysis in the clinical context that is able to finely resolve and identify those patients with cancer.

Accordingly, we herein disclose a refined method for FTIR spectral analysis to diagnose and predict cancer and, significantly and superiorly, even able to distinguish between not just healthy and cancerous individuals, but also able to distinguish pre-malignant individuals not yet exhibiting severe advanced forms of cancer (thus allowing early detection and more effective clinical treatment pathways to be applied). Therefore, such analysis provides a robust and superior diagnostic analysis that pushes the diagnostic power of FTIR analysis in cancer to a level of increased sensitivity and specificity that is a pre-requisite in any clinical diagnostic test.

STATEMENTS OF INVENTION

According to a first aspect of the invention there is provided a method for determining a preferred molecular weight fraction (MWF) of a biological sample for use in diagnosing cancer in a subject, the method comprising:

i) providing a biological sample from one or more individuals presenting with said cancer to provide one or more reference samples, and providing a biological sample from one or more individuals not presenting with said cancer to provide one or more control samples;

ii) separating each of said one or more reference samples and each of said one or more control samples based on molecular weight to provide at least two different molecular weight fractions (MWFs) for each of said one or more reference and control samples;

iii) performing Fourier transform infrared (FTIR) spectral analysis of each MWF of each reference sample to provide a plurality of reference spectra and of each MWF of each control sample to provide a plurality of control spectra;

iv) comparing the reference spectra of each MWF with the corresponding MWF of each control spectra and determining at least one diagnostic MWF(s) for said cancer by selecting at least one MWF wherein one or more differences between the reference spectra and control spectra is observed, wherein said one or more differences of said at least one diagnostic MWF(s) provide a diagnostic signature indicative of said cancer; and v) concluding that said at least one diagnostic MWF(s) is the preferred diagnostic sample for said cancer.

The invention therefore involves the identification of a specific methodology that permits separation into, and identification of, critical molecular weight fractions of biological samples from an individual that can be used to reveal key spectral differences, otherwise masked, or not observed in whole samples, achieving particularly high classification accuracy for a group of patients' diseases, and predicting diagnosis. Once determined, the best candidate MWF(s) is then identified and can be used for further diagnostic or monitoring, procedures, and other applications.

Therefore, according to a second aspect of the invention there is provided a method for determining or diagnosing cancer in a subject, the method comprising:

i) providing a biological sample from one or more individuals presenting with said cancer to provide one or more reference samples, and providing a biological sample from one or more individuals not presenting with said cancer to provide one or more control samples;

ii) separating each of said one or more reference samples and each of said one or more control samples based on molecular weight to provide at least two different molecular weight fractions (MWFs) for each of said one or more reference and control samples;

iii) performing Fourier transform infrared (FTIR) spectral analysis of each MWF of each reference sample to provide a plurality of reference spectra and of each MWF of each control sample to provide a plurality of control spectra;

iv) comparing the reference spectra of each MWF with the corresponding MWF of each control spectra and determining at least one diagnostic MWF(s) for said cancer by selecting at least one MWF wherein one or more differences between the reference spectra and control spectra is observed, wherein said one or more differences of said at least one diagnostic MWF(s) provide a diagnostic signature indicative of said cancer;

v) providing a test sample comprising a biological sample taken from a subject suspected of having or presenting with symptoms indicative of said cancer, and separating said test sample based on molecular weight to obtain said at least one diagnostic MWF(s) identified for said cancer in step iv);

vi) performing Fourier transform infrared (FTIR) spectral analysis of at least one diagnostic MWF(s) of the test sample provided in v) to provide at least one test spectra;

vii) comparing said test spectra with at least one control spectra of the corresponding MWF of said control sample and/or at least one reference spectra of the corresponding MWF of said reference sample, and where one or more difference of the diagnostic signature of step iv) is observed, concluding that said subject from which said test sample is provided is suffering from, or has an increased likelihood to be suffering from, said cancer.

Further, as will be readily appreciated by those skilled in the art, the method by which the preferred diagnostic MWF of a biological sample is determined can be completed via a first method, the results of which then being used in a second method for determining or diagnosing cancer in one or more subjects, wherein FTIR spectral analysis is performed on the diagnostic MWF of a test sample established in the first method and compared to the known FTIR spectra obtained from the same diagnostic MWF of a control sample.

Therefore, according to a third aspect of the invention there is provided a method for determining or diagnosing cancer in a subject, the method comprising:

i) providing a biological sample taken from a subject suspected of having or presenting with symptoms indicative of said cancer to provide a test sample;

ii) separating said test sample based on molecular weight to provide at least one diagnostic molecular weight fraction (MWF);

iii) performing Fourier transform infrared (FTIR) spectral analysis of at least one diagnostic MWF(s) of the test sample provided in ii), to produce a test sample spectra;

iv) comparing the test sample spectra obtained in step iii) with at least one FTIR spectra obtained from at least one control sample and/or reference sample, wherein said control and/or reference sample has also been separated based on molecular weight to provide at least one diagnostic MWF having a molecular weight cut-off the same as that of the test sample;

v) and where one or more difference is observed between the test sample spectra and at least one FTIR spectra obtained from at least one control and/or reference sample, concluding that said subject from which said test sample is provided is indicative of a subject suffering from, or having an increased likelihood to be suffering from, said cancer, wherein said at least one diagnostic MWF(s) is pre-selected according to the method of the first aspect of the invention.

In a preferred embodiment, said subject is a mammal, more preferably still human, equine, canine, feline, porcine, or any other domestic or agricultural species.

In a preferred embodiment of the invention, the biological sample may be a tissue or biopsy sample, or a processed derivative thereof. In a preferred method of the invention said biological sample is a fluid to aid the purpose of filtering. Preferably, the biological sample is not a urine sample. Ideally, the biological sample is a blood sample, including whole blood or a fraction thereof including serum and/or plasma. Reference to a processed derivative of a biological sample includes reference to a biological sample after it has been treated, typically for the purpose of pre-paring it for the method of the invention (such as in the case of a biopsy, extracting cells from the biopsy, for example by centrifugation and resuspending in an alternative medium for subsequent filtering), or preserving it prior to undertak-ing the said method and involves the use of conventional techniques well known to those skilled in the art of taking, preparing or preserving biological samples.

Reference herein to a reference sample refers to a sample provided from an individual confirmed to be suffering cancer, ideally, using any one or more conventional tech-niques for identifying same as known to those skilled in the art such as, but not limited to CT-scan, X-ray, ultrasound, MRI, biopsy, or the like.

Further, reference herein to a control sample refers to a sample provided from an individual confirmed as not having a cancer using any one or more conventional techniques for identifying same, such as those listed above and/or from a subject not yet with confirmed cancer but is observed have a pre-malignancy or pre-cancerous condition or disorder that, if left untreated, has an increased likelihood of devel-oping into cancer ideally, using any one or more of the above conventional techniques for identifying same. For example, this includes, but is not limited to: actinic keratosis, Bowen's disease, dyskeratosis congenita as skin cancer pre-malig-nancies; ductal carcinoma in situ, Sclerosing adenosis, Small duct papilloma as breast cancer pre-malignancies; oral sub-mucous fibrosis, erythroplakia, lichen planus (oral), leuko-plakia, proliferative verrucous leukoplakia, stomatitis nico-tina as head/neck/oral cancer pre-malignancies; Barrett's esophagus, atrophic gastritis, colon polyp, Plummer-Vinson syndrome (sideropenic dysphagia), hereditary nonpolyposis colorectal cancer, Ulcerative colitis, Crohn's disease as gastro-intestinal cancer pre-malignancies; cervical dysplasia (cervical intraepithelial neoplasm, CIN), vaginal intraepi-thelial neoplasm (VAIN), anal dysplasia, lichen sclerosus, Bowen's disease (penile or vulvar), erythroplasia of Queyrat as gynaecological cancer pre-malignancies; bladder carci-noma in situ as urological cancer pre-malignancy; Prostate intraepithelial neoplasia (PIN), Proliferative inflammatory atrophy (PIA), Atypical small acinar proliferation (ASAP) as prostate cancer pre-malignancies; or Mucinous cystic neoplasm (MCN), Intraductal papillary mucinous neoplasm (IPMN), Solid pseudopapillary neoplasm (SPN), Neuroen-docrine tumours as pancreatic cancer pre-malignancies.

As will be appreciated, in this manner, the method may comprise comparing spectra of reference samples to spectra of control samples obtained from healthy individuals, or those having a pre-malignancy as defined herein, and/or both. In this manner, it is possible to observe those differ-ences in reference spectra (where disease is confirmed)

compared to healthy/pre-malignant spectra i.e. to determine those differences that are indicative of cancer.

Optionally by also comparing spectra of pre-malignant individuals with healthy controls, one can add a further level of analysis by determining specifically those spectral differ-ences of a pre-cancerous disease state.

In yet a further preferred embodiment said reference sample, said control, and/or said test sample are age/gender/weight-matched.

As will be appreciated, in a preferred embodiment the nature of the sample provided for the reference, control and/or test sample is an equivalent type of sample in each case, ideally a fluid sample, such as whole blood including fractions thereof such as serum and/or plasma.

As will be known by those skilled in the art, biological samples contain a variety of molecules of varying size and molecular weight, with different abundances of different molecules. For example, blood is a particularly useful bio-fluid for routine clinical analysis due to its high protein and lipid concentration—as changes in these levels are the some of the best indicators of disease. However, when analysis is conducted on whole samples, especially with sensitive tech-niques such as spectroscopy, abundant molecules in the sample can dominate the analysis and otherwise mask potentially interesting markers/changes/observations. Therefore, in the methods of the invention, the reference, control, and test samples are separated into discrete fractions according to molecular weight, referred to herein as molecu-lar weight fractions (MWFs), with a view to categorising samples for subsequent analysis and ascertaining those fractions with particular interest, specifically in the context of cancer detection. Accordingly, the samples are separated into one or more fractions based on molecular weight to improve analytical power. Separation of samples according to molecular weight can be achieved by numerous means including, but not limited to, filtration (including ultra-filtration), size exclusion chromatography, differential cen-trifugation, density gradient centrifugation, molecular sieve chromatography, or the like.

In a preferred embodiment, the separation of samples into MWFs comprises filtering each sample provided, more preferably filtering through at least one filter membrane with a nominal molecular weight cut-off to provide at least two molecular weight fractions (MWFs) per sample in the form of the filtrate and retentate, wherein the filtrate comprises the lower molecular weight fraction relative to the retentate which comprises the higher molecular weight fraction. As will be appreciated, the molecular weight size cut-offs of the MWFs will depend according to the nominal molecular weight cut-off off (NMWCO) the filter used in filtering. As is known to those skilled in the art, NMWCO, or Molecular weight cut-off (MWCO), is a method of characterization commonly used in filtration to describe pore size distribution and retention capabilities of membranes. It is defined as the lowest molecular weight (in Daltons; Da) at which greater than 90% of a solute with a known molecular weight is retained by the membrane. As will be appreciated by those skilled in the art, the exact filter cut off can vary according to the desired MWFs of the sample being subject to analysis. In a preferred embodiment of the invention, such as wherein said sample is a fluid sample such as blood, serum, or plasma, said at least one filter has a NMWCO of between 1-100,000 Da and every integer therebetween.

In a further preferred method of the invention, the sepa-ration of samples into MWFs comprises filtering each of said samples through a plurality of filters, ideally in series, wherein each subsequent filter has a lower NMWCO with respect to the previous filter to provide a plurality of MWFs for each of the reference, test, and/or control samples. As will be appreciated, in this manner, solutes in the sample of higher molecular weight than the NMWCO will be retained on the respective filter as a retentate, and those with lower molecular weight forming the filtrate. The resulting filtrate is then filtered through each subsequent filter thus gradually forming MWFs of decreasing molecular weight cut-offs. In this manner, the retentates of each filtering step and the final filtrate represent the different MWFs of the samples.

In yet a further preferred method, the separation of samples into MWFs comprises filtering the samples with a plurality of filters each having a different NMWCO, ideally, between 1-100,000 Da and every integer therebetween. More ideally, said plurality of filters have different NMWCO selected from the group comprising: 1,000 Da, 5,000 Da, 10,000 Da, 20,000 Da, 30,000 Da, 40,000 Da, 50,000 Da, 60,000 Da, 70,000 Da, 80,000 Da, 90,000 Da, 100,000 Da, and every 100 Da therebetween, including all and any combination thereof. More ideally, said filters have a NMWCO selected from: 3,000 Da, 10,000 Da, 30,000 Da, 50,000 Da and 100,000 Da including all or any combination thereof. As will be appreciated, according to this preferred embodiment, when using a plurality of filters having these NMWCO, one can achieve MWFs of <3,000 Da, 3-10,000 Da, 10-30,000 Da, 30-50,000 Da, 50-100,000 Da, and >100,000 Da, which have been shown to represent MWF allowing improved diagnostic resolution in subsequent analysis as described herein.

As will be appreciated by those skilled in the art, due to the process of filtering there may be a gradual loss of sample volume, especially with regards to the retentate, and as such in a preferred embodiment of the method, the retentate is supplemented, before during or after filtering, with a further solution to maintain the original volume or the volume required for the execution of the subsequent method and analysis steps. Suitable solutions would be known to those skilled in the art such as, but not limited to, deionised water or any other suitable solution that can be evaporated that does not obscure spectral readings.

In a preferred method of the invention, FTIR analysis is undertaken in transmission mode which has been found to offer improved reliability. In contrast to reflectance modes (such as Attenuated Total Reflectance FTIR (ATR-FTIR)), wherein incident light is reflected and measured to provide spectral readings, in transmission mode the sample is placed directly into the infrared (IR) beam. As the IR beam passes through the sample, the transmitted energy is measured and a spectrum is generated.

As will be appreciated by those skilled in the art, in a preferred method of the invention the, or each, spectra preferably undergoes one or more conventional pre-processing steps prior to or following the comparison step to reduce the noise associated with the one or more spectra to provide the, or each, processed spectra. The pre-processing step(s) may comprise one or more of: background subtraction, and/or normalisation such as vector normalisation and/or baseline correction, or any other method known to those skilled in the art such as that of Zhang et al[12]. Given multiple reference and control spectra are obtained each spectrum is preferably subjected to one or more, preferably two or more, of wavenumber correction, baseline correction and vector normalisation.

In preferred methods, comparing reference spectra with control spectra and/or comparing test sample spectra with control spectra comprises or consists of observing one or more differences between spectra, including an increase or decrease in absorbance at the same wavenumber or a shift in position of absorbance maxima or minima between wavenumbers between the spectrum produced from the compared samples.

As will be appreciated by those skilled in the art, in a preferred method of the invention one more conventional post-processing steps are applied to like spectra to facilitate and enhance spectral comparison by separating key spectral signatures. For example, in preferred methods, said post-processing steps include one or more dimensionality reduction method such as principle component analysis (PCA). Further, the reduced spectral data may undergo support vector machine (SVM) classification or any other statistical or Machine Learning classification method to produce an individual model for each MWF from the samples selected. The model can then be tested by, e.g., a leave-one-out cross validation step to ensure there is no overfitting.

As used herein, the term "cancer" refers to cells having the capacity for autonomous growth, i.e., an abnormal state or condition characterized by uncontrolled cell proliferation. The term is meant to include all types of cancerous growths or oncogenic processes, metastatic tissues or malignantly transformed cells, tissues, or organs, irrespective of histopathologic type or stage of invasiveness.

Most preferably the cancer referred to herein includes any one or more of the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, tonsil, spleen, neuroma, von Hippel-Lindau disease, Zollinger-Ellison syndrome, adrenal cancer, anal cancer, bile duct cancer, bladder cancer, ureter cancer, glioma, oligodendroglioma, neuroblastoma, meningioma, spinal cord tumour, bone cancer, osteochondroma, chondrosarcoma, Ewing's sarcoma, cancer of unknown primary site, carcinoid, carcinoid of gastrointestinal tract, fibrosarcoma, breast cancer, muscle cancer, Paget's disease, cervical cancer, rectal cancer, esophagus cancer, gall bladder cancer, cholangioma cancer, head cancer, eye cancer, nasopharynx cancer, neck cancer, kidney cancer, Wilms' tumour, liver cancer, Kaposi's sarcoma, prostate cancer, testicular cancer, Hodgkin's disease, non-Hodgkin's lymphoma, skin cancer, mesothelioma, myeloma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

More preferably still, said cancer is selected from the group comprising the following cancers: colorectal cancer, thyroid, lymphoma, lung, liver, pancreatic, carcinoid, head & neck, stomach, urothelial, prostate, testis, endometrial, glioma, breast, cervical, ovarian, melanoma, pancreatic, liver, and renal cancers.

Yet more preferably still, said cancer is oral cancer or pancreatic cancer.

In yet a further preferred embodiment said reference sample, said control sample and/or said test sample are age/gender/weight-matched.

As will be appreciated, in a preferred embodiment the nature of the sample provided for the reference, control and test sample is an equivalent type of sample in each case, ideally a fluid sample, such as whole blood including fractions thereof such as serum and/or plasma.

According to a fourth aspect of the invention there is provided a method for determining cancer in a subject, the method comprising:

i) providing a biological sample taken from a subject suspected of having or presenting with symptoms indicative of said cancer to provide a test sample;

ii) separating said test sample based on molecular weight to provide at least one molecular weight fraction (MWF) having a molecular weight cut-off of less than 50,000 Da;

iii) performing Fourier transform infrared (FTIR) spectral analysis of at least one MWF(s) of the test sample provided in ii), to produce a test sample spectra;

iv) comparing the test sample spectra obtained in step iii) with at least one FTIR spectra obtained from at least one control sample and/or at least one reference sample, wherein at least one control sample and/or reference sample has also been separated based on molecular weight to provide at least one molecular weight fraction (MWF) having a molecular weight cut-off the same as that of the test sample;

v) and where one or more difference is observed between the test sample spectra and at least one FTIR spectra obtained from at least one control sample and/or at least one reference sample, concluding that said subject from which said test sample is provided is indicative of a subject suffering from said cancer.

In a preferred method of the fourth aspect of the invention, said sample is a fluid sample or processed derivative thereof, most ideally a blood sample, including whole blood or a fraction thereof including serum and/or plasma.

More preferably still, said test samples is separated to provide at least one MWF having a molecular weight cut-off of less than 30,000 Da, more preferably still having a molecular weight cut off selected from the group comprising: <3,000 Da, 3-10,000 Da, and/or 10-30,000 Da, which have been shown to represent MWF allowing improved diagnostic resolution in subsequent analysis as described herein.

In a further preferred method of the invention, the method comprises filtering each of said samples.

Yet more preferably still, said cancer said cancer is oral cancer or pancreatic cancer.

In a preferred embodiment of the fourth aspect of the invention, step v) comprises or consists of observing one or more differences between said test sample spectra and said control sample spectra, including an increase or decrease in absorbance at the same wavenumber or a shift in position of absorbance maxima or minima between wavenumbers between the spectrum produced from the compared sample. More preferably still, said method comprises observing a difference at one or more wavenumber ranges in any combination selected from the group comprising: 950-1000 cm$^{-1}$, 1030-1120 cm$^{-1}$, 1650-1670 cm$^{-1}$, 2840-2970 cm$^{-1}$.

In a further particular, but not exclusive, method of the fourth aspect of the invention said cancer is oral cancer, said sample is serum, and said MWF has a molecular weight cut-off between 10-30,000 Da. More preferably still, said method comprises observing a difference at one or more wavenumber ranges in any combination selected from the group comprising: 1030-1120 cm$^{-1}$, 1650 cm$^{-1}$, 2840-2970 cm$^{-1}$, most preferably 1650 cm$^{-1}$ or 2840-2970 cm$^{-1}$. In this preferred method, it was found that the 10-30 kDa subset performed better in terms of diagnostic power than whole serum (87%), producing cross validated classification accuracies of 100% for the samples used.

In a yet further particular, but not exclusive, method of the fourth aspect of the invention said cancer is pancreatic cancer, said sample is serum, and said MWF has a molecular weight cut-off selected from <10,000 Da, more preferably <3,000 Da or between 3-10,000 Da. More preferably still, said method comprises observing a difference at one or more wavenumber ranges selected from the group comprising: 950-1000 cm$^{-1}$, 1030-1120 cm$^{-1}$, or 1650-1670 cm$^{-1}$, most preferably 994 cm$^{-1}$, 1040 cm$^{-1}$ and/or 1658 cm$^{-1}$. In this preferred method, it was found that the 10-30,000 Da subset performed better than whole serum (87%), producing cross validated classification accuracies of 100% for the samples used. In this preferred method, the lower molecular weight regions produced the highest cross-validated classification accuracies. The most accurate was the <3,000 Da region, with 94% accuracy, followed by the 3-10,000 Da at 88%. Both of these were higher than the classification for whole pancreatic cancer serum, which scored only 84%.

According to a further aspect of the invention, there is provided a method for monitoring the progression of cancer in a subject comprising repeating one or more of the afore, and ideally the same, method(s) periodically.

Ideally, FTIR analysis, including the control spectra, can be correlated with known cancer staging techniques such that of a simple in vitro assay or biopsy used to reliably inform a clinician about, not only the existence of a cancer, but also its stage or progression.

As will be appreciated by those skilled in the art, in the above method of the invention comparing spectral absorbance with respect to wavenumber from the test sample and/or analyzing relative spectral difference(s) between the spectrum produced from the test sample and the control sample and/or reference sample as disclosed herein can be used to assess how effective a treatment regimen is working, for example, by assaying during the course of a given therapy to determine if there is a change in the absorbance in response to said treatment.

Additionally, or alternatively, there is provided a method for treating cancer comprising performing any one of the afore methods and then, depending upon the outcome of the method, undertaking a suitable or selected course of treatment.

Throughout the description and claims of this specification, the words "comprise" and "contain" and variations of the words, for example "comprising" and "comprises", mean "including but not limited to" and do not exclude other moieties, additives, components, integers, or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds, or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Figure 2A:
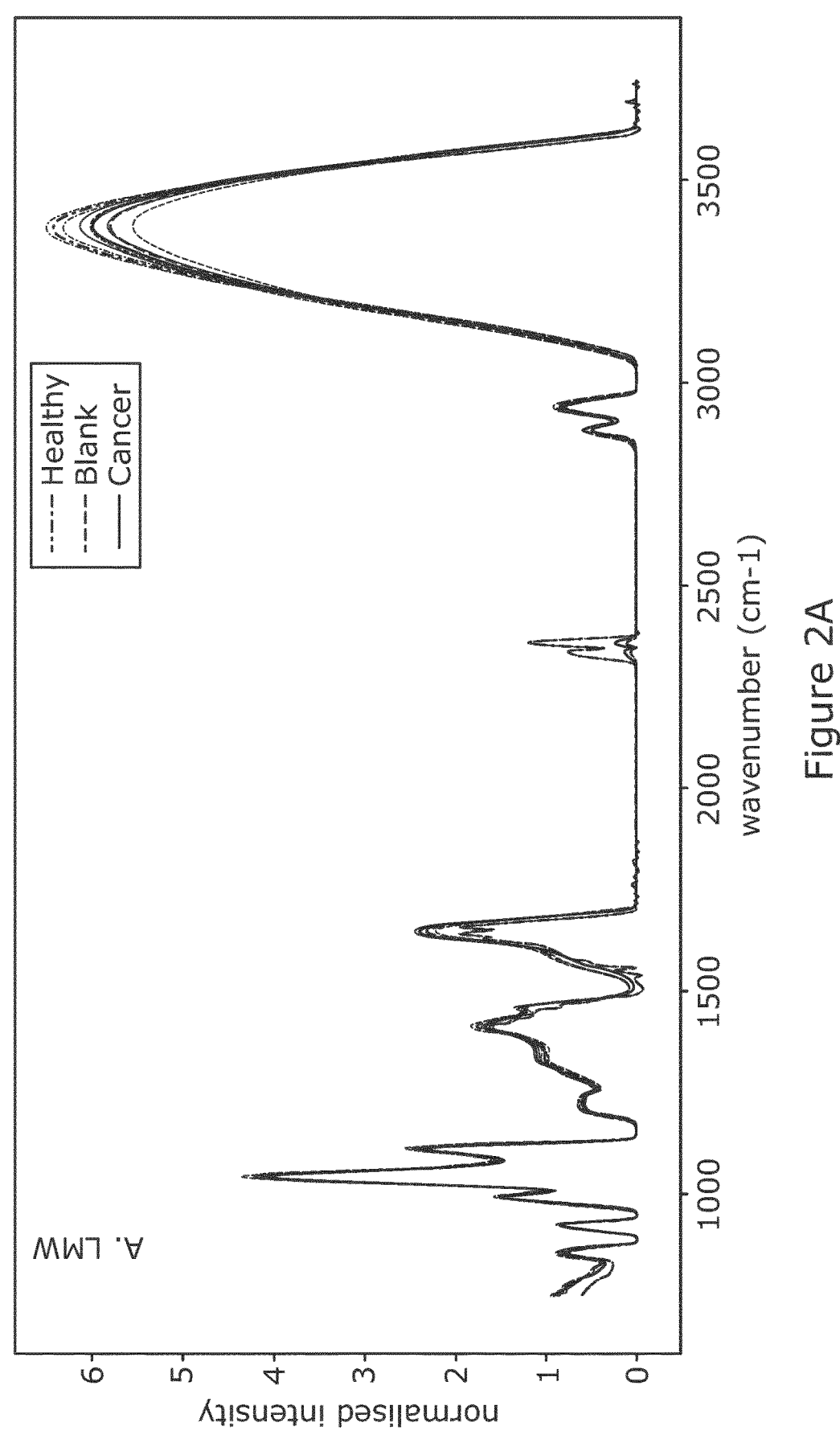
Figure 2B:
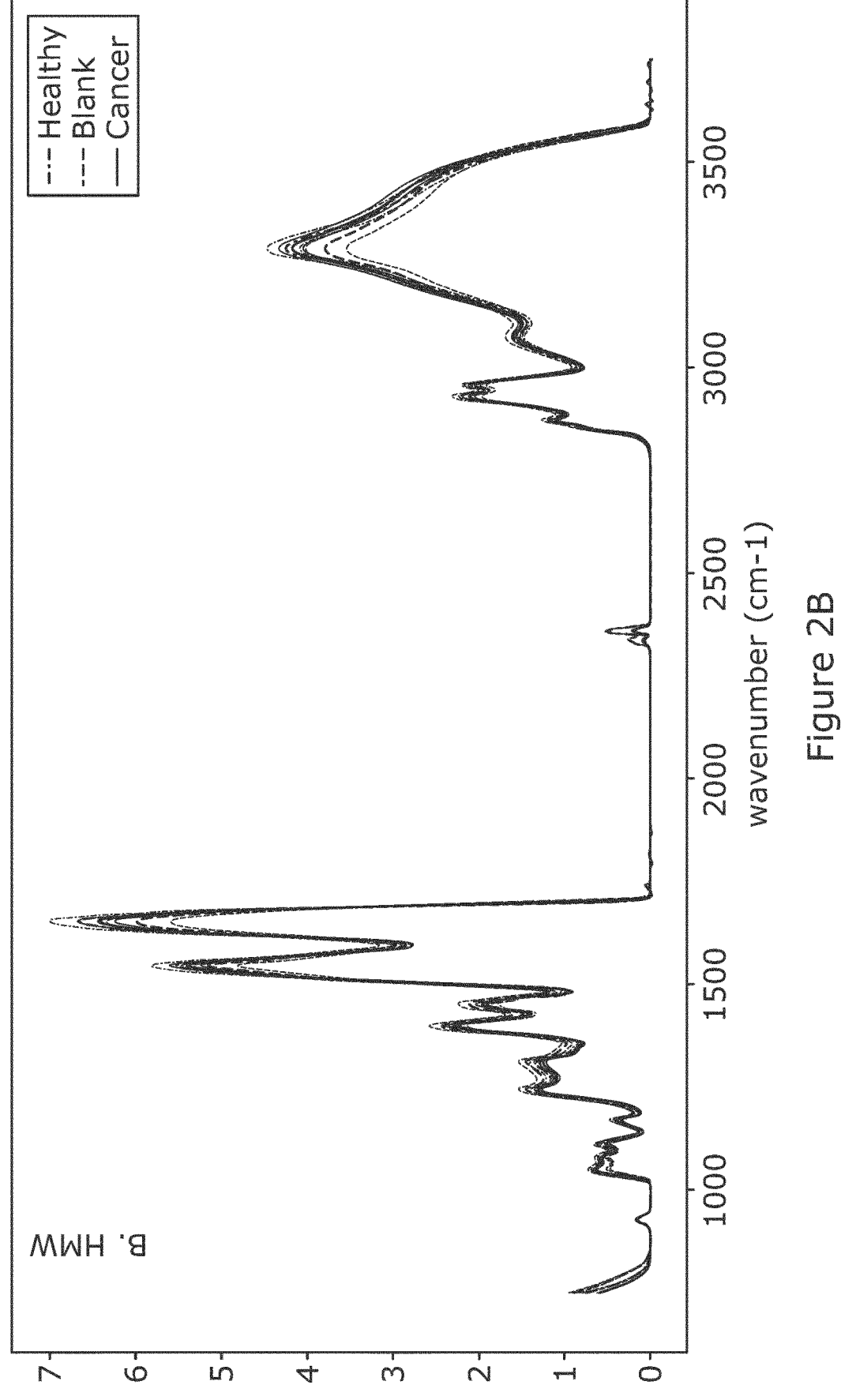
Figure 2C:
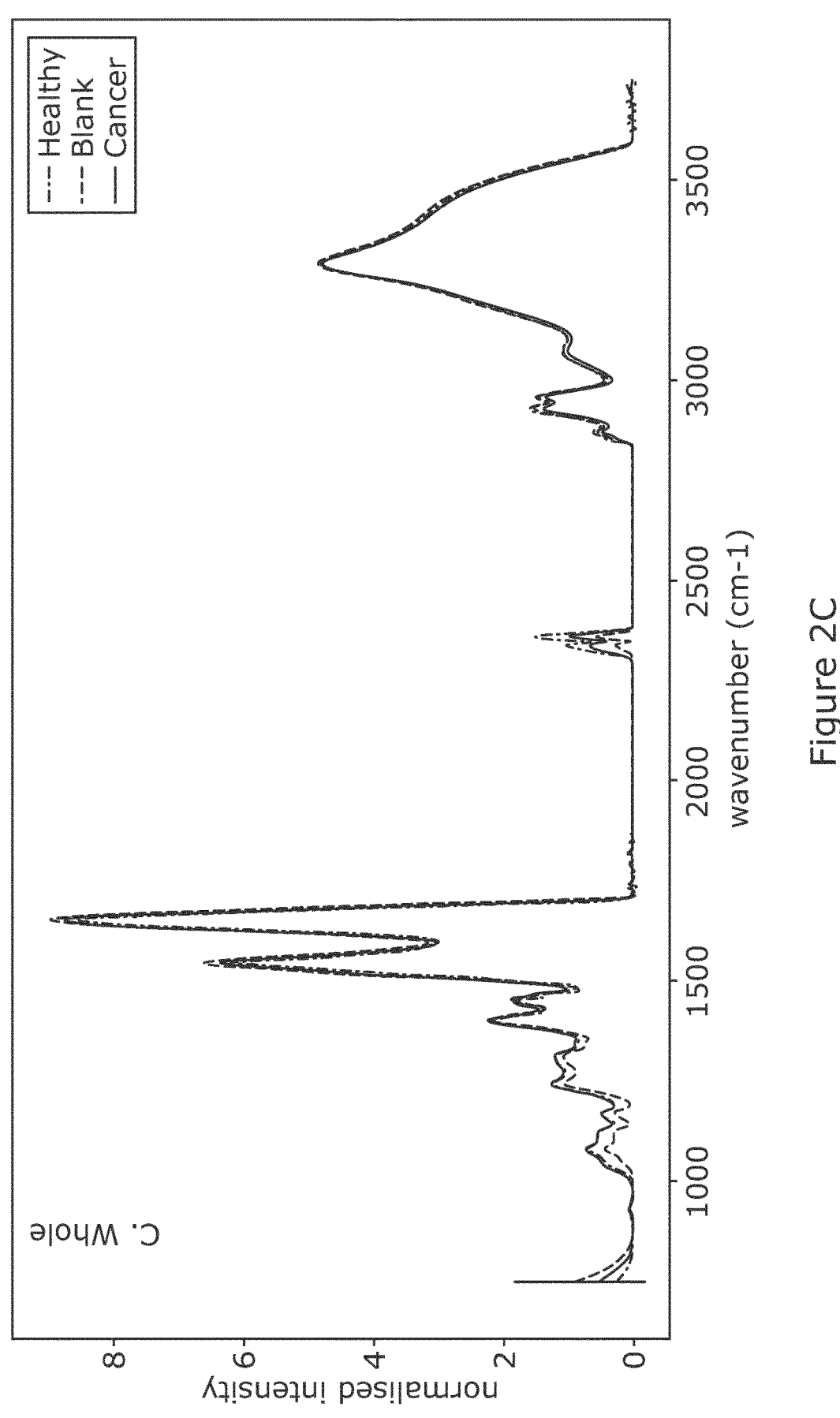
Figure 3:
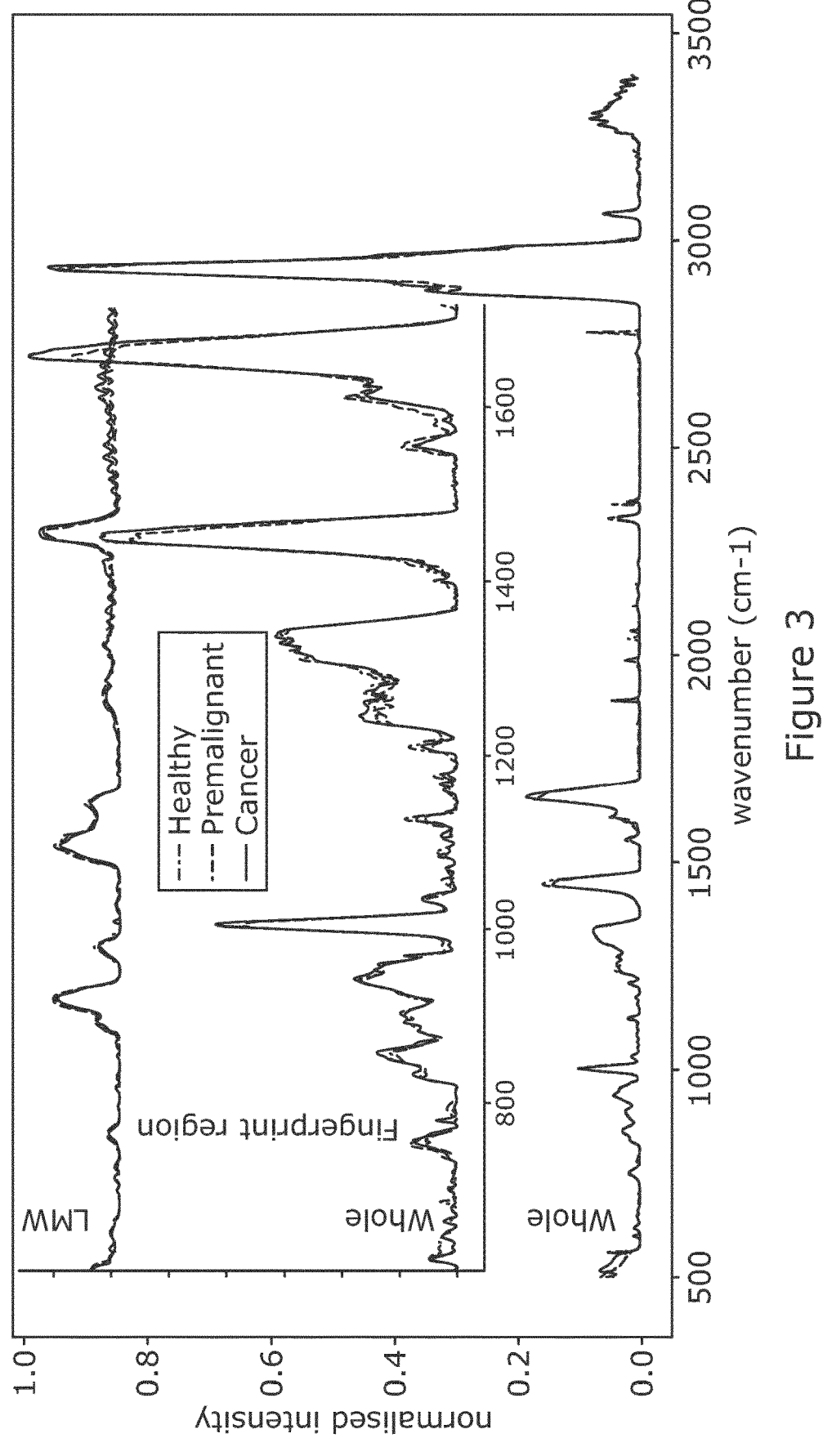
Figure 4:
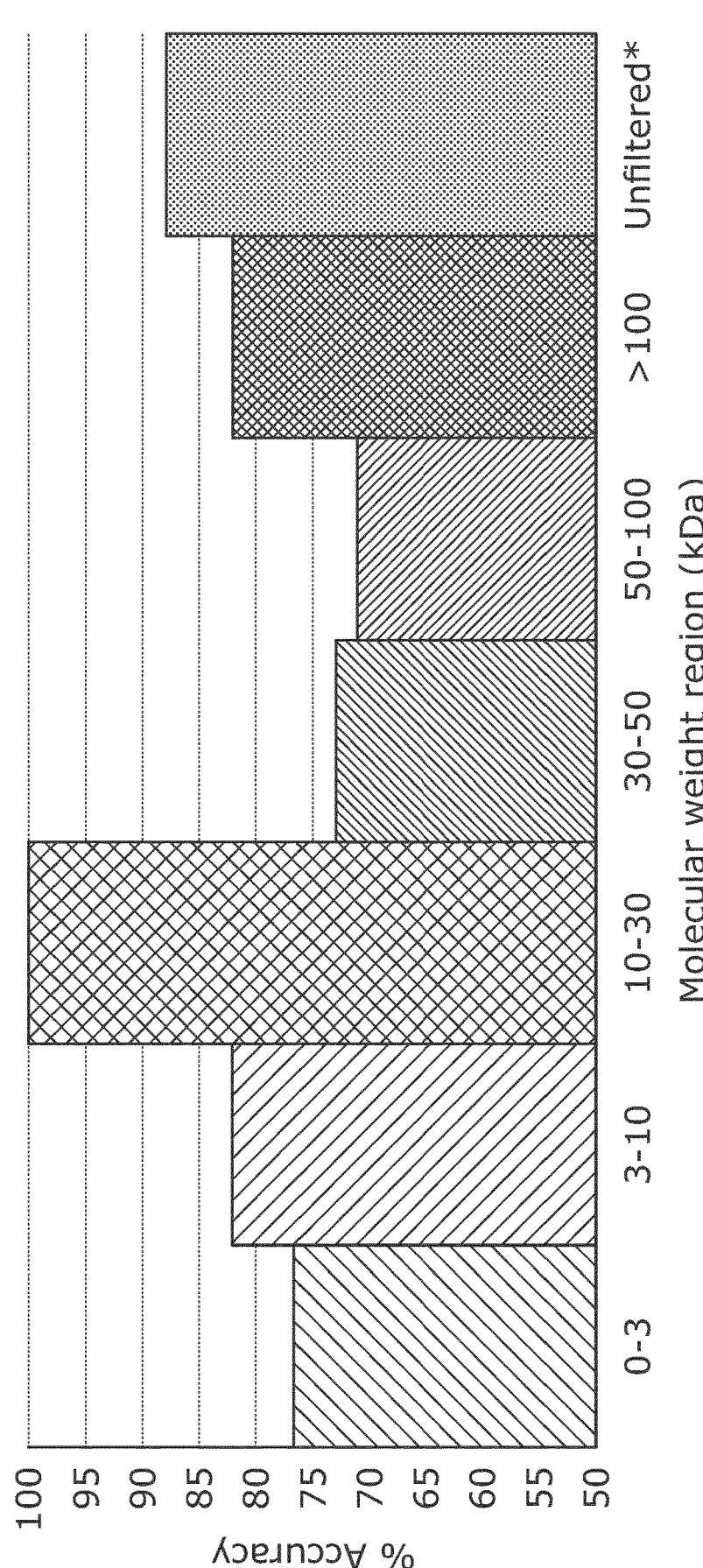
Figure 5:
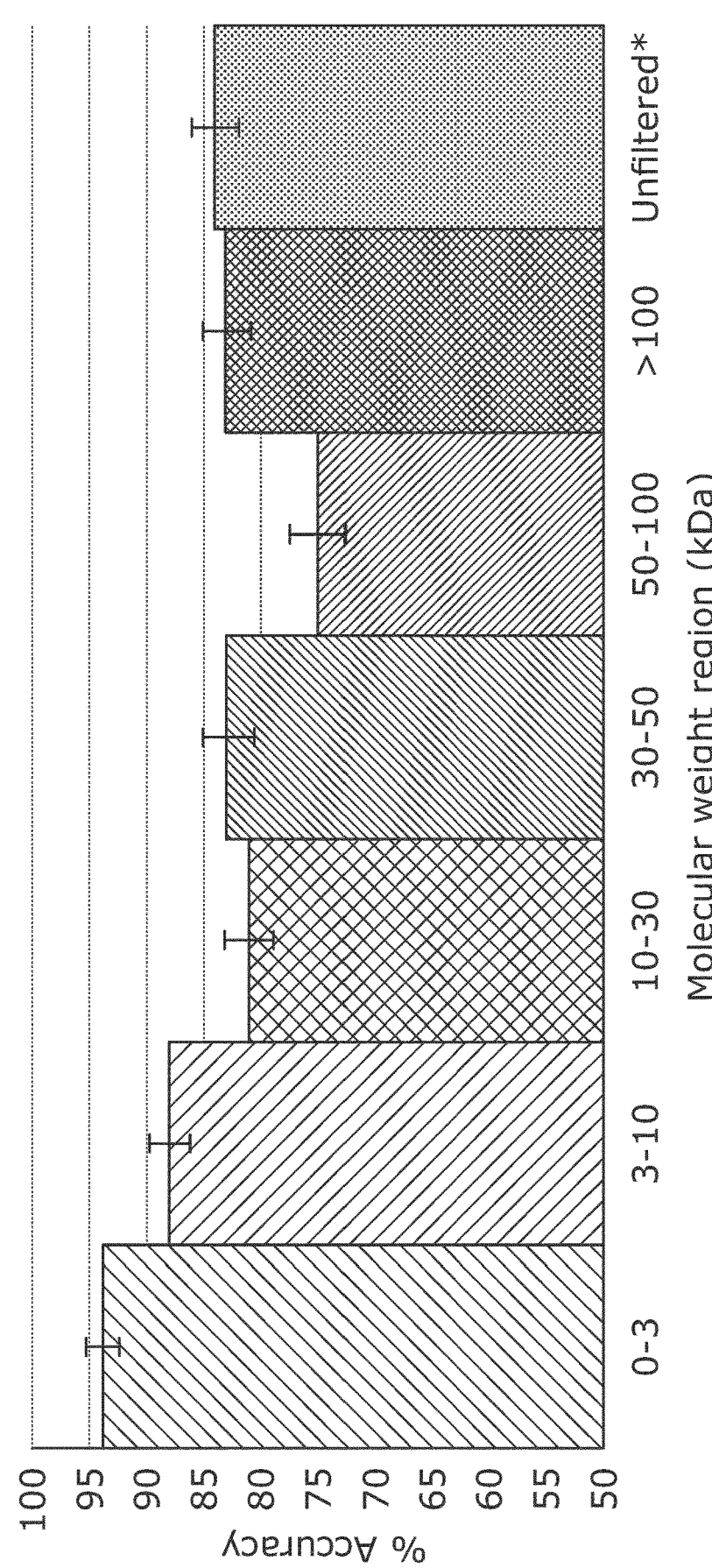
Figure 6:
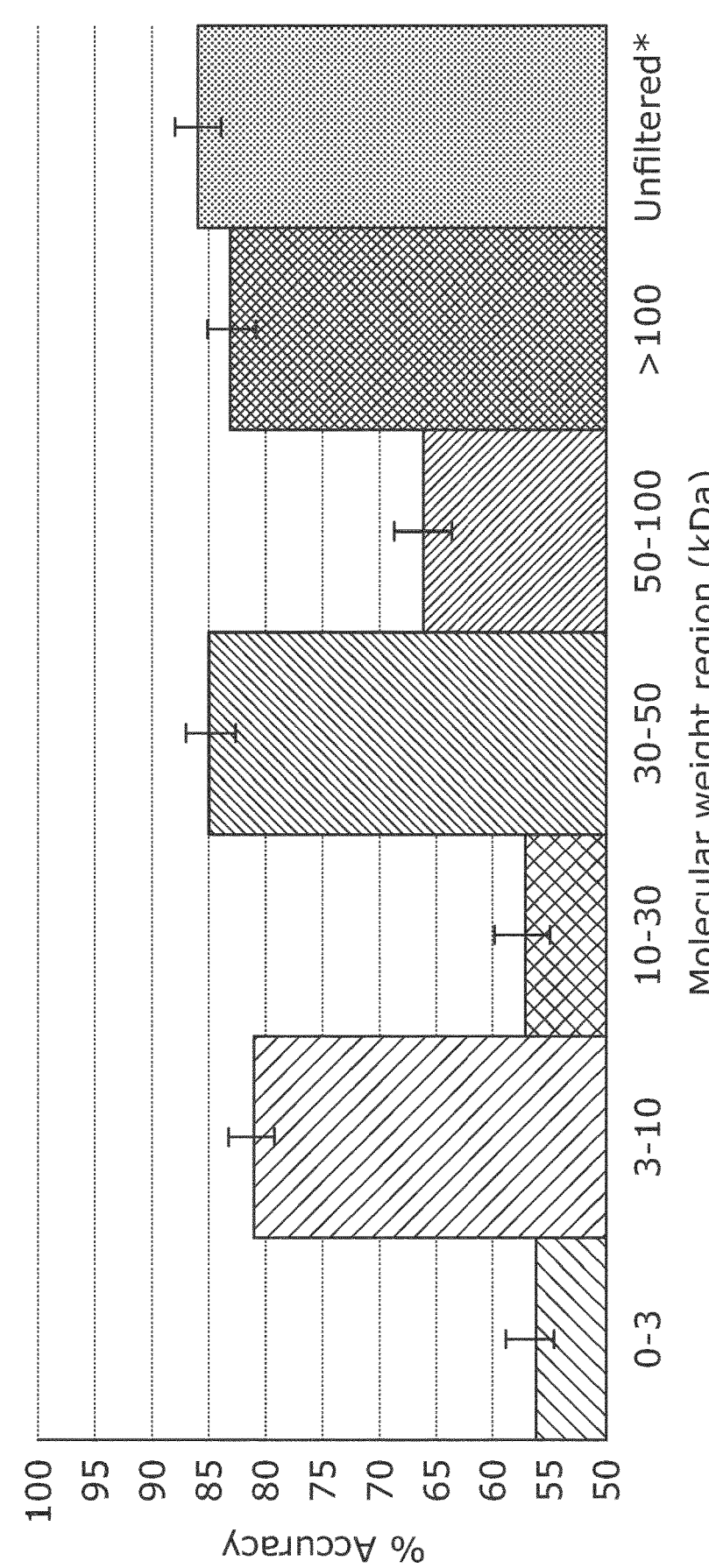

The Invention will now be described by way of example only with reference to the Examples below and to the following Figures wherein:

FIG. 1. Cross validated sensitivity and specificity values dependent on number of principle components (PCs) used in the model;

FIGS. 2A-2C. Average FTIR Spectra of the healthy, premalignant, and buccal mucosa cancer patients A) low molecular weight. Peak of interest at 1650 and 2840-2970. B) HMW. Peaks of interest at 1030-1120. C) Whole. Peaks of interest at 2840-2970;

FIG. 3. Average Raman Spectra of the healthy, premalignant, and buccal mucosa cancer patients for whole serum. No major visible deviations;

FIG. 4. Classification accuracies between FTIR spectra of premalignant and buccal mucosa cancer patients for different serum molecular weight subsets;

FIG. 5. Classification accuracies between FTIR spectra of premalignant and pancreatic cancer patients for different serum molecular weight subsets. Errors are standard binomial error calculations;

FIG. 6. Classification accuracies between FTIR spectra of pancreatic premalignant and cancer patients for different urine molecular weight subsets. Errors are standard binomial error calculations;

Table 1. FTIR cross-validation accuracy results for classifying between Buccal Mucosa Cancer (C) samples from healthy (H) and premalignant (P);

Table 2. Raman cross-validation accuracy results for classifying between Buccal Mucosa Cancer (C) samples from healthy (H) and premalignant (P);

Table-3. Comparison of serum diagnostic accuracies from subsets in the study. C: Cancer, P: Premalignant, H: Healthy, EC: Early-stage Cancer Example 1—Mouth (Buccal Mucosa) Cancer Methods Sample Preparation It is important to control for certain factors that could influence the serum spectra. Factors like age, sex, diet, certain habits i.e. smoking, pre-existing conditions or other diseases. Though little could be done to control diet in this particular experiment, efforts were made to eliminate or control for the other potentially obscuring factors.

The blood serum was collected from male patients from the TATA Cancer research hospital, Navi Mumbai, India. In the initial round, 16 had buccal mucosa cancers, 12 had premalignant oral conditions (leukoplakia) and 13 were healthy volunteers. Samples were stored at −80° C. until being thawed for analysis.

The second round was performed on a larger cohort of 90 patients: 28 oral cancer and premalignant patients as well as 17 healthy and 17 healthy tobacco users as an additional control. It should be noted that all the oral cancer patients were also tobacco users in this study.

The serum was separated into two fractions using Millipore 500 μl 50 kDa centrifugal filters. The centrifuge was run for 20 minutes at 14 kG. Whole serum, <50 kDa low molecular weight (LMW) and >50 kDa high molecular weight (HMW) fractions were analysed.

For the FTIR measurement each fraction was diluted in a 1:24 ratio of sample to MilliQ ultrapure water before 500 μl being deposited on a 25 mm diameter Crystran $CaF_2$ slide, ensuring the surface was covered to the edges, and left to dry overnight for analysis.

For the Raman measurement each fraction was diluted in a 1:3 ratio before 1 μl was deposited on a Crystran Raman grade $CaF_2$ slide and left to dry for 30 minutes.

For the molecular windowing experiment, serum samples were first filtered through 100 kDa filters, both filtrate and concentrate/retentate were collected and the filtrate was moved on to further filtering using 50, 30, 10 and 3 kDa filters until 6 subsets of serum were produced. 0-3, 3-10, 10-30, 30-50, 50-100, >100 KDa and whole serum were all analysed for comparison.

Spectral Acquisition

FTIR spectra were acquired with a Perkin Elmer spectrum 2 FTIR spectrometer used in transmission mode. Resolution was 4 $cm^{-1}$ and spectra were acquired for 5 seconds with 10 accumulations. 14 cancer, 12 premalignant and 12 healthy patients were used for this part of the study.

Raman spectra were taken using a WiTec alpha 300 spectrometer with a 532 nm laser over the relative wavenumber range −100 to 3500 $cm^{-1}$. The Resolution was 2 $cm^{-1}$, optics with a 10× magnification and 0.25 numerical aperture was used as well as a 1200 g/mm grating. Spectra were taken at a laser power of 27 mW for 10 seconds with 3 accumulations. Scans were taken over a wavenumber range of −100 to 3500 $cm^{-1}$ to investigate the entire spectra for useful signal regions, this resulted in ~24 minute acquisition times. Prior to acquisition the spectrometer was calibrated using a silica reference at 520 $cm^{-1}$. Spectra were acquired from the centre of the small, dried droplet.

Pre-Processing

Spectra were pre-processed with a background correction using the 'intelligent background correction' algorithm devised by Zhang et al.[12]. This was followed by average normalisation.

Post-Processing

Spectra were analysed by 2-factor principal component analysis linear support vector machine (PCA-SVM) classification, and sensitivity and specificity values were obtained by complete leave-one-out cross validation.

For the second run, the samples were instead analysed over a range of principle components, the resulting cross validated accuracies graphed out to find the peak sensitivity and specificity reading as shown in FIG. 1.

Results

FTIR

The produced FTIR spectra (FIGS. 2A-2C) showed clear differences between the sample groups. The cross validated sensitivity and specificity results are summarised in table 1. The separability of the groups is high all round though the HMW section is less effective. It appears that the peak around 1650 $cm^{-1}$ produced such high absorbance (>90%)

that its value is distorted and cannot be valid for mathematical comparison. Appending the spectra together increased the average accuracy in each case, though appending all three showed lower values than the LMW and Whole sets appended. This is likely due to the HMW distortion affecting the categorisation.

Looking at specific regions of deviation within the spectra it appears that the peaks around 1650 cm$^{-1}$ and 2840-2970 cm$^{-1}$ show most consistent deviation between the groups of spectra. The 1650 cm$^{-1}$ peak was higher in cancerous and premalignant patients than healthy in the LMW spectra. The peaks in the 2840-2970 cm$^{-1}$ region was lower for cancer patients than the premalignant or healthy patients in both the whole and LMW spectra. Healthy patients also show higher absorbance in the 1030-1120 cm$^{-1}$ region than the cancerous patients in the HMW and LMW spectra, but not the whole.

The FTIR results for whole serum demonstrates the ability to effectively distinguish between healthy, premalignant, and cancerous serum samples with high (>85%) accuracy. Additionally, the ability to classify using the spectra from low and high molecular weight subsets of the serum was demonstrated although no obvious benefit was evident. Therefore, we zoomed-in to narrower molecular windows to investigate further (below).

Raman

As is evident from table 2 and FIG. 3, in comparison to FTIR, the results from the Raman side of the investigation showed less clear categorisation. The LMW subset providing the worst cross validation results—averaging 46% and meaning the model used is inferior to random selection. The HMW subset and whole serum were marginally better, averaging 71% and 68% respectively. Classification seemed to be highest between cancer and premalignant samples, and lowest between cancer and healthy.

Furthermore, the addition of appending the spectra did not serve to improve the categorisation in this case, only the LMW and HMW combination producing a higher average accuracy than the average-average accuracy from the individual spectra. This data tends to suggest that the molecular weight separation has no significant improvement of diagnostic power for Raman, in comparison to FTIR as the signal is too low. Whilst adjustments, like increasing the volume of serum filtered or using a more sensitive Raman method may improve readings, these would not be feasible for screening purposes. Therefore, only FTIR was taken forward into subsequent studies.

Molecular Windowing

In the molecular windowing experiment, as shown in FIG. 4, only the 10-30 kDa subset performed better than whole serum (87%), producing cross validated classification accuracies of 100% for the samples used.

Discussion

For patient selection, a premalignant control was selected as this would best emulate a practical diagnosis scenario where the disease of interest should be discernible from similar, non-malignant diseases. A study on ovarian cancer performed this control, effectively discerning cancer patients from other benign ovarian patients. An additional healthy control is also used as a reference and to potentially allow quantification of the cancer severity if patient outcomes are monitored. Gender was controlled by only male patients being selected for this initial study to help reduce unintentional bias.

The intelligent baseline correction algorithm was chosen for its renown and effectiveness. Average normalisation was used so that variation in all the peaks could be assessed. Linear PCA-SVM and complete leave-one-out cross validation were chosen as the dataset was small enough for complete cross validation, linear SVM produced the best classification for our dataset, and SVM is highly, and sometimes the most, effective in studies.

The FTIR results, in contrast to Raman, demonstrated the ability to effectively distinguish between healthy, premalignant, and cancerous serum samples with high accuracy. Additionally, the ability to distinguish the spectra from low and high molecular weight subsets of the serum was demonstrated. Without wishing to be bound to theory, it is thought that key small molecules were being obscured by the larger proteins when considered in whole serum. However, the classification is still present from a majorly different low molecular weight spectra, as it reduces the contribution of albumin, globulin, and other high weight components. Therefore, there is definitely valuable information to be gleaned from this subset. Furthermore, the identification of the 10-30 kDa region as providing the best overall classification accuracy suggests that the molecular weight splitting can still have value, especially if this particular region is exploited.

For this Buccal Mucosa case, the peaks at 1030-1120 cm$^{-1}$, 1650 cm$^{-1}$, 2840-2970 cm$^{-1}$ were noted as key variations. The 1030-1120 cm$^{-1}$ region varies inconsistently between samples and subsets. It is close to the edge of the FTIRs detection range and consequently close to the edge of the baseline correction and therefore it is possible that some minor but category consistent fluctuations may have been amplified by errors in this. It perhaps deserves further investigation, but no valid conclusions can be drawn from this data alone.

The 1650 cm$^{-1}$ peak is likely the Amide 1 peak. This is very strong in the HMW and whole spectra. The observed shifts between groups in the LMW spectra is likely obscured by the same peak from contributions from large molecules in the other spectra. However, this shift is consistent between the premalignant and cancer patients and therefore is likely from increases in inflammatory or similar general disease response molecules produced by the body to defend from potentially any illness, and not cancer specific.

The 2840-2970 cm$^{-1}$ peak is most of note as it only reduces in the cancerous samples, meaning it may well be a cancer specific biomarker. It is also only seen in the LMW and whole sets, meaning it is likely from a contribution from the <50 kDa molecules and therefore not present in the HMW set. There are several candidates for the peak's molecular origins; C—H stretching from aldehydes and several other bonds, as well as N—H stretching form bonded quaternary amine salts.

There are no significant known Buccal Mucosa biomarkers in common medical use today. FTIR on this identified window produces a new spectral biomarker that could be used as a diagnostic tool and to narrow down efforts to find additional novel biomarkers.

Example 2—Pancreatic Cancer

Pancreatic cancer was chosen for this UK based study as it is one of the most prevalent cancers that is hard to confirm in patients without invasive, costly procedures. Urine was looked at in additions to blood serum as it is also non-invasively collected and could potentially have parallels in the present biomarkers.

Methodology

Sample Preparation

The blood serum and urine was collected from the same cohort of patients from Morriston hospital, Swansea, UK. For the full cohort plasma experiment, 17 had late-stage pancreatic cancer (C), 14 had early-stage (EC), 10 were healthy (H) and 33 had premalignant pancreatic conditions (P). For the windowing experiment, 9 had Severe pancreatic cancer and were compared to patients who had premalignant pancreatic conditions. Samples were stored frozen until being thawed for analysis.

Each biofluid sample was first filtered through a 100 kDa filter, both filtrate and concentrate/retentate being collected, and the filtrate being moved on to further filtering using 50, 30, 10 and 3 kDa filters until 6 subsets of serum were produced. 0-3, 3-10, 10-30, 30-50, 50-100, >100 kDa and whole serum were all analysed for comparison. For the full cohort, only a 10 kDa filter was used, both whole and <10 kDa plasma being analysed.

For the FTIR measurement each fraction was diluted in a 1:24 ratio of sample to MilliQ ultrapure water before 500 μl being deposited on a 25 mm diameter Crystran $CaF_2$ slide, ensuring the surface was covered to the edges, and left to dry overnight for analysis.

Spectral Acquisition

FTIR spectra were acquired with a Perkin Elmer spectrum 2 FTIR spectrometer used in transmission mode. Resolution was 4 $cm^{-1}$ and spectra were acquired for 5 seconds with 4 accumulations.

Pre-Processing

Spectra were pre-processed with a background correction using the ALSS method[13]. This was followed by average normalisation.

Post-Processing

Spectra were analysed over a range of principle components followed by linear support vector machine (PCA-SVM) classification, and sensitivity and specificity values were obtained by complete leave-one-out cross validation. Classification accuracy was also obtained from spectra for each of the different molecular weight fractions.

Results and Discussion

Classifying cancer and healthy patients is relatively straightforward. We believe that the main challenge lies in eliminating the standard inflammatory and other general disease markers from the premalignant conditions that deteriorate the diagnosis accuracy of cancer as both cancer as well as premalignant patients reach out to clinicians with similar symptoms. For this experiment, only cancer and premalignant patients were chosen for the initial run, as they are both the hardest and most key groups to differentiate. This is due to the presence of standard inflammatory and other general disease classifiers being present in both of these samples that would serve to differentiate them from healthy samples. Furthermore, in a diagnostic scenario, it is unlikely for a patient to be seeking this without any symptoms, and therefore being able to distinguish cancer from other benign signals is essential. For screening purposes, a healthy control set would also be used.

In the blood serum molecular windowing experiment, as shown in FIG. 5, the lower molecular weight regions produced the highest cross-validated classification accuracies. The most accurate was the <3 kDa region, with 94% accuracy, followed by the 3-10 kDa at 88%. Both of these were higher than the classification for whole pancreatic cancer serum, which scored 84%. For practical purpose and ease of implementation, we designed our study to probe the <10 kDa filtrate. From Table 3, we can see that the <10 kDa filtrate performed better than whole plasma for all comparisons made, each has higher than 92% accuracy when diagnosing late-stage patients against healthy and premalignant pancreatic patients. Furthermore, when early-stage cancer patients were included, 90% accuracy was still achieved The urine data (FIG. 6) performed worse overall, unfiltered urine scoring the maximum at 86%, with results from >100 and 30-50 kDa scoring within error of that.

The results can be compared to currently used ELISA methods using the known pancreatic cancer biomarker Carbohydrate Antigen 19-9 (CA19-9), which produced 70-80% accuracy on the same patient samples. This biomarker is in the same weight range as the optimal FTIR region. However, the patients misclassified by each method were different. Furthermore, when the filtered subsets were subjected to the same ELISA test, they exhibited low levels of the biomarker. This indicates the spectral biomarker is unrelated to CA19-9, and CA 19-9 is attached and filtered out with heavier molecules.

From these results, one can conclude that using either just the <3 kDa region or even expanding to the <10 kDa molecular weight region can potentially provide a superior classifier model to using unfiltered serum alone. Furthermore, urine can be used as a diagnostic biofluid, but the accuracy would not be as high as when serum is used. Resultingly, FTIR on this identified window produces a novel spectral biomarker that could be used as a diagnostic tool.

SUMMARY

The method analyses key molecular weight bands from biological fluids from patients with Fourier Transform Infrared Spectroscopy (FTIR) to produce and utilise a superior differential diagnostic model of their disease(s). The ideal bands for each disease are first discovered by performing a full weight range test of the fluid, separating the bands by, e.g., repeated ultrafiltration.

The potential of FTIR for screening for cancer is demonstrated by this study, as well as the additional use of ultra-filtration to further the categorisation accuracy and provide more information about the signal's origins. Furthermore, the molecular windowing section of this showed even greater promise from its even higher classification accuracy.

This refined method for FTIR spectral analysis and signature determination to diagnose and predict cancer and, significantly and superiorly, with the capacity not just able to distinguish between healthy and cancerous individuals, but also able to distinguish pre-malignant individuals not yet exhibiting severe advanced forms of cancer (thus allowing early detection and more effective clinical treatment pathways to be applied). Therefore, such analysis provide a robust and superior diagnostic analysis that pushes the diagnostic power of FTIR analysis in cancer to a level of increased sensitivity.

TABLE 1

| | Cancer/Healthy | | | Cancer/Premalignant | | | Premalignant/Healthy | | | Average |
| Sample | Sensitivity | Specificity | Accuracy | Sensitivity | Specificity | Accuracy | Sensitivity | Specificity | Accuracy | Accuracy |
|---|---|---|---|---|---|---|---|---|---|---|
| LMW | 92% | 94% | 93% | 95% | 91% | 93% | 90% | 100% | 95% | 94% |
| HMW | 88% | 83% | 86% | 69% | 63% | 66% | 71% | 90% | 81% | 77% |
| Whole | 92% | 83% | 88% | 90% | 77% | 84% | 95% | 93% | 94% | 88% |

TABLE 2

| | Cancer/Healthy | | | Cancer/Premalignant | | | Premalignant/Healthy | | | Average |
| Sample | Sensitivity | Specificity | Accuracy | Sensitivity | Specificity | Accuracy | Sensitivity | Specificity | Accuracy | Accuracy |
|---|---|---|---|---|---|---|---|---|---|---|
| LMW | 56% | 38% | 47% | 62% | 50% | 56% | 30% | 41% | 36% | 46% |
| HMW | 56% | 61% | 59% | 93% | 91% | 92% | 61% | 66% | 64% | 71% |
| Whole | 68% | 46% | 57% | 81% | 66% | 74% | 69% | 75% | 72% | 68% |

TABLE 3

Comparison of serum diagnostic accuracies
from subsets in the study.

| Fraction | Subsets compared | Sens. | Spec. | % Acc. |
|---|---|---|---|---|
| Whole serum | C v P | 89 | 89 | 89 |
| | C v H | 91 | 92 | 91.4 |
| | C v H + P | 78 | 91 | 87.2 |
| | C + EC v H + P | 82 | 92 | 87.7 |
| <10 kDa window | C v P | 92 | 94 | 93 |
| | C v H | 96 | 95 | 95.5 |
| | C v H + P | 85 | 95 | 92.4 |
| | C + EC v H + P | 91 | 89 | 89.8 |

C: Cancer,
P: Premalignant,
H: Healthy,
EC: Early-stage Cancer

REFERENCES

12 Zhang, Z. M. et al. An intelligent background-correction algorithm for highly fluorescent samples in Raman spectroscopy. Journal of Raman Spectroscopy 41, 659-669, doi:10.1002/jrs.2500 (2009).
13 Eilers, P. & Boelens, H. Baseline Correction with Asymmetric Least Squares Smoothing.

The invention claimed is:

1. A method for detecting oral cancer or pancreatic cancer in a subject, comprising:
   i) providing a biological sample taken from a subject suspected of having or presenting with symptoms indicative of the oral cancer or pancreatic cancer to provide a test sample;
   ii) separating said test sample based on molecular weight to provide at least one molecular weight fraction (MWF) having a molecular weight cut-off of less than-30,000 Da;
   iii) performing Fourier transform infrared (FTIR) spectral analysis of at least one MWF(s) of the test sample provided in ii), to produce a test sample spectra;
   iv) comparing the test sample spectra obtained in step iii) with at least one FTIR spectra obtained from at least one control sample and/or at least one reference sample, wherein at least one control sample and/or reference sample has also been separated based on molecular weight to provide at least one molecular weight fraction (MWF) having a molecular weight cut-off the same as that of the test sample;
   v) observing where one or more differences between the test sample spectra and at least one FTIR spectra obtained from at least one control sample and/or at least one reference sample, and
   vi) concluding that said subject from which said test sample is provided is indicative of a subject having oral cancer or pancreatic cancer.

2. The method according to claim 1, wherein step v) comprises observing a difference at one or more wavenumber ranges in any combination selected from the group consisting of 950-1000 cm$^{-1}$, 1030-1120 cm$^{-1}$, 1650-1670 cm$^{-1}$, and 2840-2970 cm$^{-1}$.

3. The method of claim 1, wherein,
   the method is a method for detecting oral cancer, said sample is serum, and said at least one MWF has a molecular weight cut-off between 10-30,000 Da.

4. The method of claim 3, wherein the method further comprises observing a difference at one or more wavenumber ranges in any combination selected from the group consisting of: 1030-1120 cm$^{-1}$, 1650 cm$^{-1}$, and 2840-2970 cm$^{-1}$.

5. A method for monitoring the progression of oral cancer or pancreatic cancer in a subject, comprising repeating the method according to claim 1.

6. The method of claim 1, further comprising treating the oral cancer or pancreatic cancer in the subject with a suitable or selected course of treatment.

7. The method of claim 1, further comprising treating the oral cancer or pancreatic cancer in the subject with a suitable or selected course of treatment.

8. The method of claim 1, wherein the biological sample is a tissue or biopsy sample, or a processed derivative thereof.

9. The method of claim 8, wherein the biological sample is a fluid.

10. The method of claim 1, wherein separation of the samples comprises filtration, size exclusion chromatography, differential centrifugation, density gradient centrifugation, and/or molecular sieve chromatography.

11. The method of claim 10, wherein separation of samples into at least one MWF comprises filtering each sample provided.

12. The method of claim 11, wherein the method comprises filtering through at least one filter membrane with a nominal molecular weight cut-off to provide at least two MWFs per sample in the form of the filtrate and retentate, wherein the filtrate comprises the lower molecular weight fraction relative to the retentate which comprises the higher molecular weight fraction.

13. The method of claim 11, comprising filtering each of said samples through a plurality of filters, wherein each subsequent filter has a lower NMWCO with respect to the previous filter to provide a plurality of MWFs for each of the reference, test and/or control samples.

14. The method of claim 13, comprising filtering the samples with a plurality of filters each having a different NMWCO selected from the group consisting of 1,000 Da, 5,000 Da, 10,000 Da, 20,000 Da, and 30,000 Da, and every 100 Da therebetween, including all and any combinations thereof.

15. The method of claim 13, wherein filtering each of said samples through a plurality of filters is performed in series.

16. The method of claim 1, wherein the, or each, spectra undergoes one or more conventional pre-processing steps prior to or following the comparison step to reduce the noise associated with the one or more spectra to provide the, or each, processed spectra.

17. The method of claim 16, wherein the post processed spectra undergo support vector machine (SVM) classification or any other statistical or Machine Learning classification method to produce an individual model for each MWF from the samples selected.

18. The method of claim 1, wherein one more conventional post-processing steps are applied to like spectra to facilitate and enhance spectral comparison by separating key spectral signatures.

19. The method of claim 18, wherein the post processed spectra undergo support vector machine (SVM) classification or any other statistical or Machine Learning classification method to produce an individual model for each MWF from the samples selected.

20. The method of claim 1, wherein the method is a method for detecting pancreatic cancer, said sample is serum, and said at least one MWF has a molecular weight cut-off of <10,000 Da.

21. The method of claim 20, wherein the method further comprises observing a difference at one or more wavenumber ranges selected from the group consisting of: 950-1000 $cm^{-1}$, 1030-1120 $cm^{-1}$, and 1650-1670 $cm^{-1}$.

22. The method of claim 1, wherein the filtration comprises ultra-filtration.

\* \* \* \* \*